United States Patent [19]

Barkhoudarian

[11] Patent Number: 5,235,524
[45] Date of Patent: Aug. 10, 1993

[54] ULTRASONIC CAVITATION DETECTION SYSTEM

[75] Inventor: Sarkis Barkhoudarian, Canoga Park, Calif.

[73] Assignee: Rockwell International Corporation, Seal Beach, Calif.

[21] Appl. No.: 502,945

[22] Filed: Apr. 2, 1990

[51] Int. Cl.$^5$ .............................................. G01N 29/02
[52] U.S. Cl. ...................................... 364/506; 73/168
[58] Field of Search ............... 364/506, 508, 555, 560, 364/574, 575; 73/587, 590, 168; 367/141; 128/660.01

[56] References Cited

U.S. PATENT DOCUMENTS

| | | | |
|---|---|---|---|
| 3,538,747 | 11/1970 | Munch | 73/590 |
| 3,557,354 | 1/1971 | Trimble | 364/574 |
| 3,608,715 | 9/1971 | Snyder et al. | 73/590 |
| 3,622,765 | 11/1971 | Anderson | 364/575 |
| 3,910,216 | 10/1975 | Shultz | 367/141 |
| 4,058,004 | 11/1977 | Hammitt et al. | 73/590 |
| 4,089,055 | 5/1978 | Dyer et al. | 364/508 |
| 4,412,451 | 11/1983 | Uusitalo et al. | 73/599 |
| 4,819,621 | 4/1989 | Ueberle et al. | 128/660.01 |
| 4,909,076 | 3/1990 | Busch et al. | 73/590 |

FOREIGN PATENT DOCUMENTS 2200991 8/1988 United Kingdom ................. 73/590

OTHER PUBLICATIONS

De Etul; "Instrument System for Monitoring Cavilation Noise"; Journal of Physics; vol. 15 1982.

*Primary Examiner*—Kevin J. Teska
*Assistant Examiner*—Ellis B. Ramirez
*Attorney, Agent, or Firm*—H. Fredrick Hamann; Harry B. Field

[57] ABSTRACT

A forced-excitation ultrasonic cavitation detection system for detecting cavities in rotating machinery such as pumps, water turbines and ducting elements, is composed of an ultrasonic transmitting transducer attached to the outer wall of the test component for transmitting ultrasonic pulses into the test component, and at least one, and preferably a plurality of ultrasonic receiving transducers attached to the outer wall of the test component for receiving the ultrasonic pulses passing through the test component. The ultrasonic transmitting transducer is excited by an ultrasonic pulse generator. An electronic data processing system is provided which is connected to the output of the receiving transducers and is also connected to the ultrasonic pulse generator through a synchronization line. The data processing system is programmed to discriminate as between signals from the receiving transducers due to cavitation in the test component, from other extraneous signals including noise. For this purpose the data processing system includes an algorithm, such as ensemble averaging, time-gating or cross-correlation, each capable of extracting signals due to cavitation from noise signals even of much higher intensity. When there is no cavitation, a maximum signal is received. In the presence of cavitation, as by the presence of vapor or gas bubbles, this interferes with the propagation of the pulses, thus reducing the amplitude of the received signal.

7 Claims, 1 Drawing Sheet

ULTRASONIC CAVITATION DETECTION SYSTEM

BACKGROUND OF THE INVENTION

1. Field of the Invention

This invention relates to the detection of cavitation in rotating machinery, and is particularly concerned with a system for detecting cavitation in turbomachinery and ducts, using forced-excitation ultrasonic means.

2. Description of the Prior Art

Unstable vapor pockets, known as cavities, form in rotating machinery whenever the difference in velocity head and hydrostatic pressure of the fluid therein falls below the vapor pressure of the liquid. These cavities collapse and cause erosion.

Cavitation erosion is a major problem in chemical and power-plant operations. It occurs commonly in turbomachinery including both pumps and water turbines, as well as valves, elbows and other ducting elements, and this leads to equipment damage and expensive plant unavailability. In the operations of such plants, a pump/turbine may go from noncavitating to cavitating conditions when one or more parameters such as speed, flow-rate, inlet pressure, and vapor pressure (due to weather) are changed. Detecting a severely cavitating condition prior to hardware damage and/or pump hydraulic head breakdown would greatly enhance smooth plant operation.

Most of conventional cavitation detection methods are undesirable in plant environments. Dye tests require costly disassembly and reassembly of equipment. Optical methods require windows, which can break or become soiled, creating potential hazards and establishing the need for frequent inspection, maintenance, repair or replacement. Microphones and hydrophones have problems distinguishing between cavitation noise and background noise, often creating a false or ambiguous signal. Hence, these technologies are not suitable for long-term, continuous cavitation monitoring of plants. Furthermore, since many of these detectors are not portable or retrofitable, their routine maintenance requires costly facility shutdowns.

SUMMARY OF THE INVENTION

To overcome the limitations and disadvantages of conventional cavitation detection methods and system, according to the invention a forced-excitation ultrasonic cavitation detection system is provided. This system utilizes ultrasonic transducers mounted on a test component and an intelligent electronic data-processing system designed for detecting cavitation in the test component in response to ultrasonic pulses passed through the test component and to the resulting signals received from the ultrasonic transducers. The intensity of the received signals provides a measure of the level of cavitation.

Thus, broadly, according to the invention, there is provided a forced-excitation ultrasonic cavitation detection system which comprises a test component, an ultrasonic transmitting transducer mounted on said test component for transmitting ultrasonic pulses into said component.

at least one receiving transducer mounted on said test component and spaced from said transmitting transducer for receiving the ultrasonic pulses passing through said test component, and electronic data processing means to provide the degree of cavitation in said component in response to the intensity of the signal received from said at least one receiving transducer.

According to a feature of the invention, an electronic data processing system is provided for processing signals from the receiving transducers and programmed to discriminate signals due to cavitation in the test component from other extraneous signals including noise signals, to thereby provide the degree of cavitation in the test component in response to the intensity of only those signals resulting from such cavitation. For this purpose, certain algorithms are employed in the electronic data processing system, as described in greater detail below, for processing the received signals to provide the degree of cavitation in the test component.

OBJECT OF THE INVENTION

It is accordingly one object of the present invention to provide an improved cavitation detection system for rotating machinery.

Another object is the provision of an ultrasonic cavitation detection system for turbomachinery including pumps, turbines and ducting elements.

A further object is to provide a forced-excitation ultrasonic cavitation detection system for test components of the above type, including data processing means to provide the degree of cavitation in response to the intensity of signals generated due to such cavitation.

Yet another object is the provision of the above forced-excitation ultrasonic cavitation detection system including a data processor which is programmed to discriminate between signals due to cavitation and extraneous or spurious signals such as noise.

Other objects and advantages of the invention will be apparent or made obvious by the description below of certain preferred embodiments of the invention.

DETAILED DESCRIPTION OF THE INVENTION AND PREFERRED EMBODIMENTS

Figure 1:
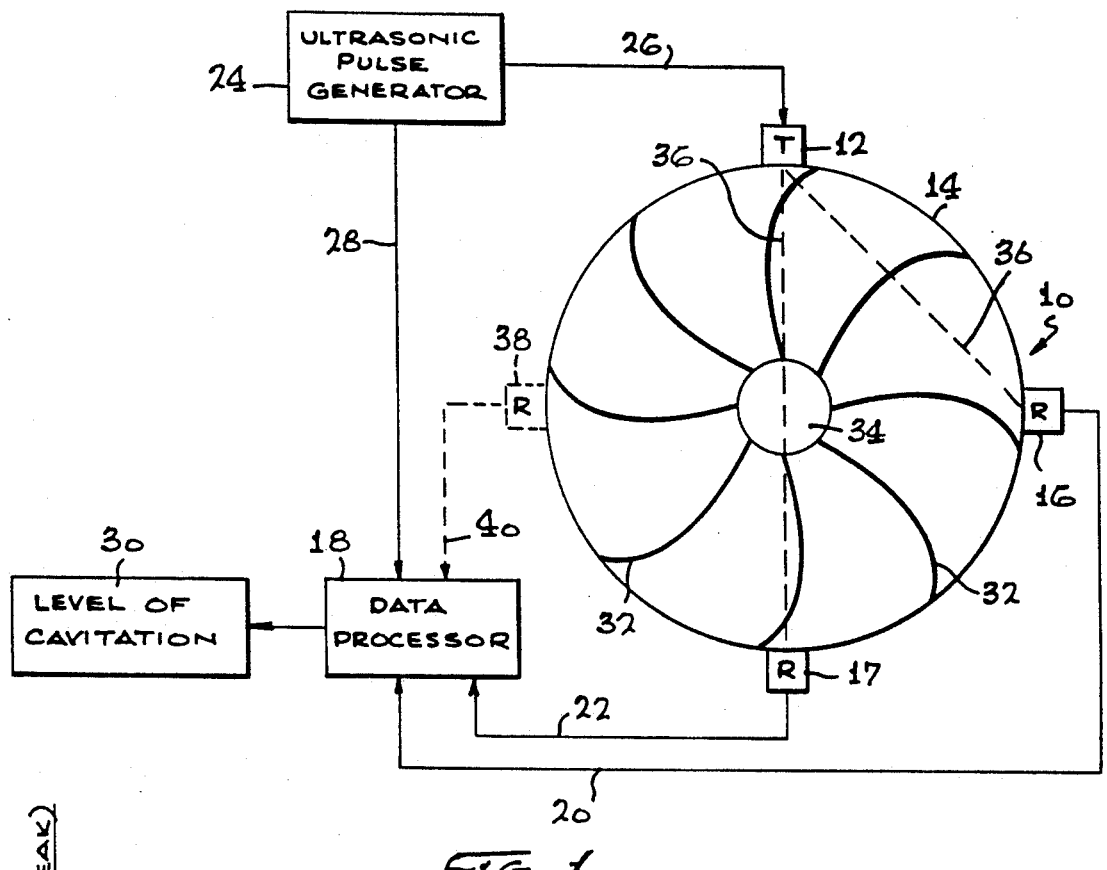
FIG. 1 is a schematic illustration of a forced-excitation ultrasonic cavitation detection system according to the invention.

Referring to FIG. 1 of the drawing, illustrating a forced-excitation ultrasonic cavitation detection system according to the invention, numeral 10 indicates a test component in the form of a pump. The system employs ultrasonic transducers, attached to the test component and an intelligent data-processing system designed for detecting cavitation in such test component.

Thus, in forced-excitation ultrasonics, according to the invention, an ultrasonic transmitting transducer 12 is attached, as by clamping or by permanent attachment to the outer wall or periphery 14 of the pump. A plurality of ultrasonic receiving transducers 16 and 17 are also similarly mounted on the outer periphery or wall of the pump, the receiving transducers 16 and 17 being spaced from each other and from the transmitting transducer 12. In the present embodiment one of the transmitting transducers 16 is located at a position 90° from transmitting transducer 12 and the second receiving transducer 17 is disposed diagonally opposite transmitting transducer 12. The positioning of the receiving transducers 16 and 17 can be varied as desired with respect to the transmitting transducer 12. A data processor or electronic data processing system 18 is connected to the receiving transducers 16 and 17 via lines 20 and 22, respectively. An ultrasonic pulse generator 24 is connected via line 26 to the transmitting transducer 12 for exciting same, and is also connected via a synchronization line 28 to the data processor 18.

The ultrasonic pulse generator 24, and the transmitting transducer 12 and the receiving transducers 16 and 17 are conventional components. The transmitting transducer 12 can be a piezoelectric transmitter or a magnetostrictive transmitter, and the receiving transducers 16 and 17 can be piezoelectric receivers or magnetostrictive receivers.

In operation, the ultrasonic pulse generator 24 excites the transmitting transducer 12, which sends ultrasonic pulses into the pump through the pump housing 14, liquid therein (not shown), blades 32, and shaft 34, and any other internal elements, to the receiving transducers 16 and 17, as shown by the ultrasonic paths 36. The ultrasonic pulse generator 24 employs a frequency substantially higher than the background hydrodynamic or structural noise spectrum. Thus, frequencies of 100 kHz or higher have been used to avoid interference from spontaneously emitted mechanical and hydrodynamic background noise, which is typically lower than 20 kHz. Simultaneously with excitation of transducer 12, a clocking pulse is transmitted by the pulse generator 24 to the data processor 18, via the synchronization line 28. When there is no cavitation, the ultrasonic pulses propagate through the liquid and internal elements of the pump to the receiving transducers 16 and 17, resulting in a maximum signal or voltage. In the presence of cavitation, vapor or gas bubbles interfere with the propagation of the ultransonic pulses, thus reducing the amplitude (voltage) of the received signal.

The ultrasonic pulse generator 24 employs a pulse shape which is optimized according to each system. These pulse shapes can be burst-shaped, consisting of several identical pulses; ramp-shaped, consisting of several pulses of the same frequency but different amplitude; or chirp-shaped, consisting of several pulses of different frequency and/or different amplitude.

The data processor 18 incorporates an algorithm to process the signals received from the receiving transducers 16 and 17 to indicate the degree or level of cavitation at 30 in the component. The data processor 18 is programmed to discriminate between the received signals due to cavitation and those which are not, such as other extraneous signals, e.g. background noise. For this purpose, the data processor incorporates a suitable algorithm.

Various algorithms which can be used to process the data received from the receiving transducers 16 and 17 in the system illustrated in FIG. 1 include ensemble averaging, time-gating, or cross-correlation procedure, which are capable of extracting signals due to cavitation from as much as 10-fold larger intensity noise signals. These are all well known types of data processing procedures. In ensemble averaging, also known as stacking, multiple signals are superimposed. The cavitation signals interfere constructively while the random noise signals interfere destructively, resulting in signal enhancement due to cavitation and reduction of signals due to noise. In this procedure time domain or frequency domain are different types of ensemble averaging which can be employed.

With a time-gating process, signals not arriving within an appropriate time interval, measured from excitation time, are filtered out, eliminating undesirable signals carried by the pump housing wall which arrive sooner due to the higher speed of sound in metals than in liquids, and eliminating reflections from blades, housing interior or other internal elements such as shaft and seals, due to the longer path traveled by these signals.

The cross-correlation procedure is used to enhance the reliability of measurement by identifying the signal shape. Undesirable multiple-reflected or housing-wall transmitted signals, as well as hydrodynamic and structural noises may combine to produce confusing signals, which could arrive within the proper time interval. These signals are eliminated through the use of cross-correlation algorithms if their shapes differ from uniquely shaped excitation pulses such as burst-shaped or chirp-shaped.

All of the above algorithms are different data-processing techniques for determining whether or not cavitation is present in the test component. They each permit differentiation as between signals due to cavitation and other signals such as noise, and the strength of such signals due to cavitation. If the intensity of the processed signal in the embodiment of FIG. 1, for example, is reduced, this indicates that bubbles have been generated behind the blades of the pump and cavitation exists. Thus, the forced-excitation ultrasonic technology of the present invention benefits significantly from the use of the above data-processing techniques in minimizing false signals and enhancing the reliability of measurements.

Figure 2:
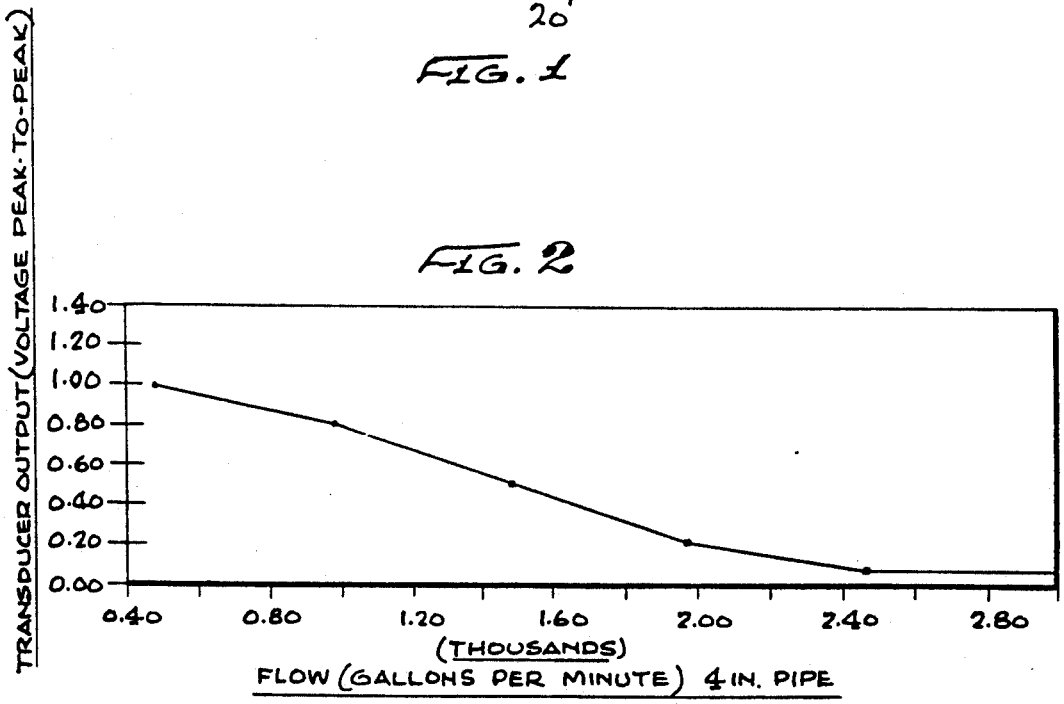
FIG. 2 is a plot illustrating cavitation effects on signal strength transducer output as a function of cavitation.

Referring to FIG. 2 of the drawing, this further illustrates the principle of the present invention employing forced-excitation ultrasonic cavitation detection in a pipe. FIG. 2 is a plot of output voltage from a forced excitation ultrasonic cavitation system of the type illustrated in FIG. 1, for determining cavitation effects based on rate of fluid flow in a 4-inch pipe. Thus, it is seen that as the flow rate increases in the pipe, a reduction in voltage or strength of the received signal occurs, indicating an increase in cavitation with increased fluid flow, as observed through a 4 inch Plexiglas sighting pipe section. This illustrates that a decrease in the ultrasonic signal results when cavitation is increased.

It will be understood that various modifications of the ultrasonic cavitation detection system of the invention can be made. Thus, while a single receiving transducer can be employed, it is preferred to employ a multiplicity of receiving transducers at various locations on the test component to enhance the signal to noise ratio. While the use of two receiving transducers is shown in FIG. 2, more than two such transducers can be employed. Thus, for example, an additional transducer indicated in dotted lines at 38 located on the peripheral wall 14 of the pump diagonally opposite receiving transducer 16, can be employed, and connected to the data processor 18 by a line 40. As many as 5 to 10 receiving transducers can be employed depending on the complexity of the structure of the test component. If only one receiving transducer is employed it is preferred to place such transducer on one side of the peripheral wall 14, as illustrated by the receiving transducer 16 located 90° from the transmitting transducer 12, so as to avoid having to transmit ultrasonic pulses through the shaft 34 of the pump, as would be the case if the sole receiving transducer were positioned at the location of transducer 17.

It is also possible to employ a multiplicity of transmitting transducers in place of the single transmitting transducer 12 shown in FIG. 1. For example where a single transmitting transducer 12 is employed with the three receiving transducers 16, 17 and 38 shown in FIG. 1, if it is desired to obtain more information on the periphery of the pump, several more receiving transducers would be required. The same result can be achieved by mounting another transmitting transducer 12 on the periphery 14 spaced from the first transducer, without increasing the number of receiving transducers. When employing two transmitting transducers with the three receiving transducers as shown in FIG. 1, only one transmitting transducer is fired at a time and after that pulse has been received by the receiving transducers, then the other transmitting transducer is fired and the resulting ultrasonic pulse is received by the same set of receiving transducers. This, thus provides two sets of signal information.

From the foregoing, it is seen that the invention provides an ultrasonic cavitation detection system which overcomes the limitations and disadvantages of conventional cavitation detection methods, employing a system of ultrasonic transducers attached to a test component, in combination with an intelligent data-processing system designed for accurately detecting cavitation in the test component.

It is to be understood that what has been described is merely illustrative of the principles of the invention and that numerous arrangements in accordance with the invention may be devised by one skilled in the art without departing from the spirit and scope thereof.

What is claimed is:

1. A forced-excitation ultrasonic cavitation detection system which comprises
    a turbomachine,
    an ultrasonic transmitting transducer attached to the outer wall of said turbomachine for transmitting ultrasonic pulses into said turbomachine,
    an ultrasonic pulse generator for forced excitation of said ultrasonic transmitting transducer,
    a plurality of ultrasonic receiving transducers attached to the outer wall of said turbomachine, for receiving the ultrasonic pulses passing through said turbomachine, and
    an electronic data processing system for processing signals from said receiving transducer and programmed to discriminate signals due to cavitation in said turbomachine from other extraneous signals including noise, to thereby indicate the level of cavitation in said turbomachine corresponding to the intensity of the signals due to cavitation,
    said ultrasonic pulse generator connected to said data processing system through a synchronization line.

2. The cavitation detection system of claim 1, employing a plurality of said ultrasonic transmitting transducers attached to the outer wall of said turbomachine and spaced from each other and from said receiving transducers.

3. The cavitation detection system of claim 1, said turbomachine including pumps, turbines, and ducts.

4. The cavitation detection system of claim 1, said ultrasonic pulse generator employs a frequency substantially higher than the background hydrodynamic or structural noise spectrum.

5. The cavitation detection system of claim 1, wherein said data processing system employs an algorithm to process the received signals and to indicate the level of cavitation in said turbomachine corresponding to the intensity of the signals due to cavitation and discriminating from said other extraneous signals.

6. The cavitation detection system of claim 5, said algorithm comprising ensemble averaging.

7. The cavitation detection system of claim 5, said algorithm comprising time-gating.

* * * * *